United States Patent [19]
Jacobsen et al.

[11] Patent Number: 5,931,830
[45] Date of Patent: *Aug. 3, 1999

[54] HOLLOW COIL GUIDE WIRE APPARATUS FOR CATHETERS

[75] Inventors: Stephen C. Jacobsen; Clark Davis, both of Salt Lake City, Utah

[73] Assignee: Sarcos L.C., Salt Lake City, Utah

[*] Notice: This patent issued on a continued prosecution application filed under 37 CFR 1.53(d), and is subject to the twenty year patent term provisions of 35 U.S.C. 154(a)(2).

[21] Appl. No.: 08/569,017

[22] Filed: Dec. 7, 1995

[51] Int. Cl.⁶ .................................................. A61M 25/00
[52] U.S. Cl. ............................................. 604/523; 604/264
[58] Field of Search .................................... 128/657, 772; 604/95, 280–282; 600/435, 585, 434

[56] References Cited

U.S. PATENT DOCUMENTS

| | | |
|---|---|---|
| 4,884,579 | 12/1989 | Engelson . |
| 4,955,862 | 9/1990 | Sepetka . |
| 4,994,069 | 2/1991 | Ritchart et al. . |
| 5,125,395 | 6/1992 | Adair ............................................ 128/4 |
| 5,365,942 | 11/1994 | Shank ....................................... 128/772 |
| 5,437,288 | 8/1995 | Schwartz et al. . |
| 5,438,993 | 8/1995 | Lynch et al. . |
| 5,441,483 | 8/1995 | Avitall . |
| 5,441,489 | 8/1995 | Utsumi et al. . |
| 5,666,969 | 9/1997 | Urick et al. .............................. 128/772 |
| 5,682,894 | 11/1997 | Orr et al. ................................. 128/654 |

FOREIGN PATENT DOCUMENTS

PCT/US92/
07619   9/1992   WIPO .

*Primary Examiner*—Wynn Wood Coggins
*Assistant Examiner*—Deborah Blyveis
*Attorney, Agent, or Firm*—Thorpe, North & Western LLP

[57] ABSTRACT

A catheter guide wire includes a strip of material formed into an elongate coil, with a central hollow having a plurality of windings. The windings include inhibiting features to inhibit relative rotation of adjacent windings. A central wire core is inserted through the hollow of the coil and welded to some of the windings to keep them from separating longitudinally. This construction allows for lateral flexibility of the guide wire, but with desired torsional stiffness.

16 Claims, 2 Drawing Sheets

HOLLOW COIL GUIDE WIRE APPARATUS FOR CATHETERS

BACKGROUND OF THE INVENTION

This invention relates to catheter systems and more particularly to hollow guide wire apparatus with improved torque and flexure characteristics.

Catheter guide wires have been used for many years to "lead" or "guide" catheters to desired target locations in the human body's vasculature. The typical guide wire is from about 135 centimeters to 195 centimeters in length, and is made from two primary pieces—a stainless steel solid core wire, and a platinum alloy coil spring. The core wire is tapered on the distal end to increase its flexibility. The coil spring is typically soldered to the core wire at its distal end and at a point where the inside diameter of the coil spring matches the outside diameter of the core wire. Platinum is selected for the coil spring because it provides radiopacity for X-ray viewing during navigation of the guide wire in the body, and it is biocompatible. The coil spring also provides softness for the tip of the guide wire to reduce the likelihood of puncture of the anatomy.

Navigation through the anatomy is achieved by viewing the guide wire in the body using X-ray fluoroscopy. The guide wire is inserted into a catheter so the guide wire protrudes out the end, and then the wire and catheter are inserted into a vessel or duct and moved therethrough until the guide wire tip reaches a desired vessel or duct branch. The proximal end of the guide wire is then rotated or torqued to point the curved tip into the desired branch and then advanced further. The catheter is advanced over the guide wire to follow or track the wire to the desired location, and provide additional support for the wire. Once the catheter is in place, the guide wire may be withdrawn, depending upon the therapy to be performed. Oftentimes, such as in the case of balloon angioplasty, the guide wire is left in place during the procedure and will be used to exchange catheters.

As the guide wire is advanced into the anatomy, internal resistance from the typically numerous turns, and surface contact, decreases the ability to advance the guide wire further. This, in turn, may lead to a more difficult and prolonged procedure, or, more seriously, failure to access the desired anatomy and thus a failed procedure. A guide wire with both flexibility and good torque characteristics (torsional stiffness) would, of course, help overcome problems created by the internal resistance.

SUMMARY OF THE INVENTION

It is an object of the invention to provide an improved catheter guide wire apparatus.

It is also an object of the invention to provide such apparatus which exhibits both torsional stiffness, bending flexibility, and longitudinal strength.

It is a further object of the invention to provide such apparatus which is simple in design and construction.

The above and other objects of the invention are realized in a specific illustrative embodiment of a catheter guide wire apparatus which includes a strip of material formed into an elongate coil, with central hollow, having a plurality of windings. Also included are inhibiting elements formed in or on at least certain adjacent windings for inhibiting rotation of the windings relative to one another. The coil construction allows for lateral flexibility of the guide wire apparatus, while the inhibiting elements provide torquability, i.e., torsional stiffness, to allow transmission of torque along the coil. A central wire mandrel may be inserted through the hollow of the coil and welded to some of the coils to keep the coils from separating.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
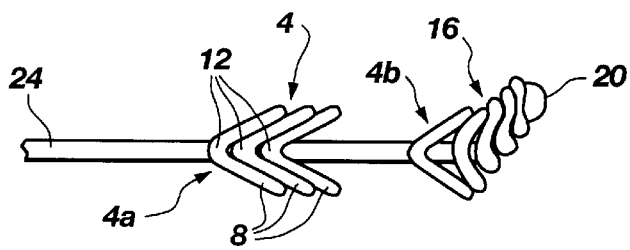
FIG. 1 is a side, fragmented view of one embodiment of a catheter guide wire apparatus made in accordance with the principles of the present invention.

Referring to FIG. 1, there is shown a side, fragmented view of a catheter guide wire in the form of an elongate coil 4 having a plurality of windings 8. At least some of the windings 8 are formed with adjacent, interlocking bends 12, which inhibit relative rotational movement of adjacent windings. Because of the coil construction, the coil 4 is laterally flexible to enable guiding it around curves and bends in vessels and ducts in the human body. The bends 12 in the windings give the coil 4 torquability so that rotating a proximal end 4a of the coil transmits torque along the length of the coil to a distal end 4b of the coil.

The distal end 4b of the coil is formed with a curved tip 16, the end of which includes a solder ball 20 or similar blunt tip for the coil. The curved tip 16 allows for guiding the guide wire around curves and bends, as previously discussed. Alternatively, the tip 16 could be made of a shapeable material to initially be straight, so that the user could later curve the tip as desired.

A central mandrel or core wire 24, which may be tapered and/or curved, is inserted through the center of the coil 4 and soldered or welded (e.g. by laser welding) to at least some of the coils to prevent the coils from separating longitudinally so that torquability can be maintained. The core wire can also serve to control the flexibility of the coil, i.e., stiffen the coil to a greater or lesser extent depending upon the needs of the user. In this manner, the flexibility of the coil can be varied and controlled.

After or while the guide wire coil 4 is being inserted in a vessel, a catheter would be threaded about the exterior of the coil to be guided to the desired destination location.

The outside diameter of the coil 4 might illustratively be from 0.008 inches to 0.090 inches, with a length of about 1 centimeter to 50 centimeters. Advantageously the coil 4 is made of platinum alloy, nickel-titanium alloy or stainless steel to provide the desired strength, radiopacity and biocompatibility.

Figure 2:
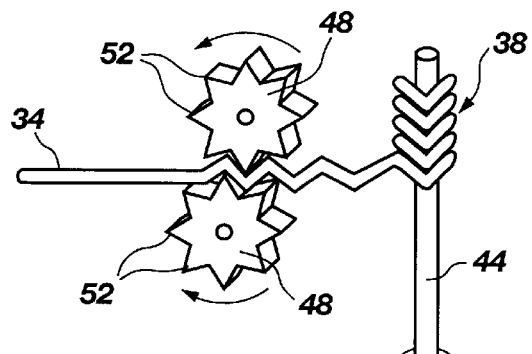
FIG. 2 illustrates diagrammatically a method of producing a herringbone coil guide wire apparatus in accordance with the present invention.

FIG. 2 illustrates diagrammatically a method of forming bends or a herringbone pattern in a length of wire 34 which is then formed into a coil 38 about a mandrel 44. The bends are formed by moving the wire 34 lengthwise between a pair of rotating wheels 48 formed with teeth 52. The wheels 48 are rotated in the directions indicated so that, to a certain extent, the teeth 52 of the wheels intermesh to form bends in alternating directions as the wire 34 is moved between the wheels. The wire 34 with bends is then wrapped on a mandrel 44 so that the bends of adjacent windings interlock, as indicated, after which the mandrel is removed.

Figure 3:
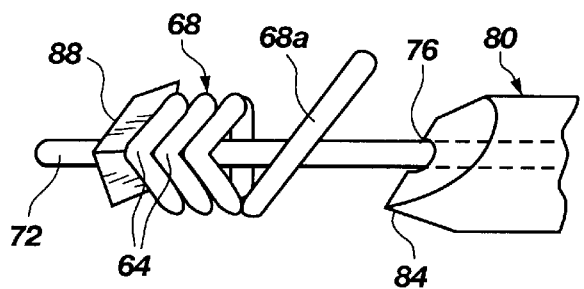
FIG. 3 illustrates another method of producing a coil guide wire apparatus with bends, in accordance with the present invention.

FIG. 3 diagrammatically shows an alternative method of producing bends 64 in a wire coil 68. Here, a mandrel 72 is threaded both through the coil 68 and through a center opening 76 in a hammer 80. The hammer 80 includes a wedge-shaped tip 84 so that when the hammer is moved along the mandrel 72 into contact with a length of wire 68a which is not yet bent, the hammer forces the length against a previously bent winding to thereby bend the length to conform to the previously formed bends. (The initial winding bent by the hammer 80 would have been forced against an anvil 88, rigidly mounted on the mandrel 72 and bent at the same angle desired for the coil bends 64.) After each winding is bent by the hammer 80, the hammer is withdrawn and the mandrel 72 rotated to position the next length of wire to be bent. After all bends are formed in the wire coil 68, the coil may be held in the coiled position and heat treated to "set" the bends in the coil.

Figure 4:
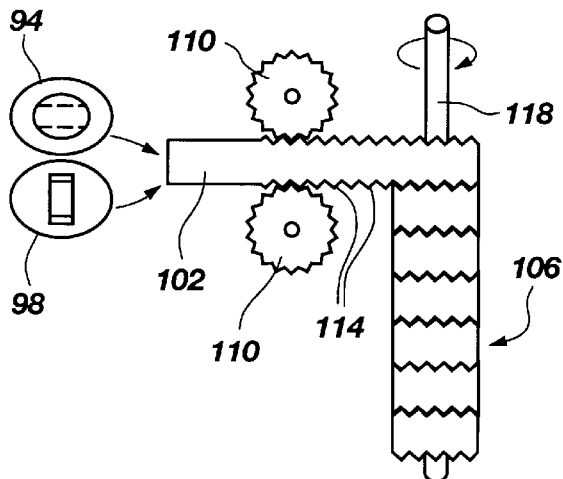
FIG. 4 shows another method of producing either a cylindrical, flat or square strip with serrated edges, for formation into a guide wire coil apparatus in accordance with the present invention.

FIG. 4 shows an alternative embodiment of a coil guide wire formed either from round wire (shown in cross-section at 94), flat wire (shown at 98 in cross-section) or square wire. The wire 102 to be formed into the coil 106 is passed between toothed wheels 110 which impress and form teeth 114 on opposite edges of the wire 102 as shown. The wire 102 is then wound about a mandrel 118 so that the teeth on adjacent edges of the wire intermesh or interlock, as also shown in FIG. 4, to provide the inhibiting mechanism to inhibit relative rotation of adjacent windings of the coil 106. The mandrel 118 may be maintained in the coil 106 as a core wire, after the coil is finished being formed, and soldered or welded to various coils to keep them from separating.

Figures 5A, 5B:
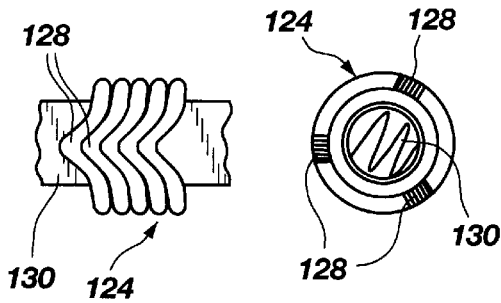
FIGS. 5A and 5B show respectively a side, fragmented view of a coil guide wire apparatus having interlocking ears, and an end view of the apparatus wire.

FIGS. 5A and 5B show respectively a side, fragmented view of a coil guide wire 124, and a front end view. Formed at three spaced-apart locations around each winding is an ear or nipple 128 protruding longitudinally to nest with adjacent ears or nipples, as shown. The nesting of the ears 128 provides the inhibiting mechanism for relative rotation of one winding with respect to adjacent windings to thereby provide for increased torsional stiffness. A core wire 130 is inserted in the hollow of the coil 124 and welded or soldered to various coils as earlier described.

Figure 6:
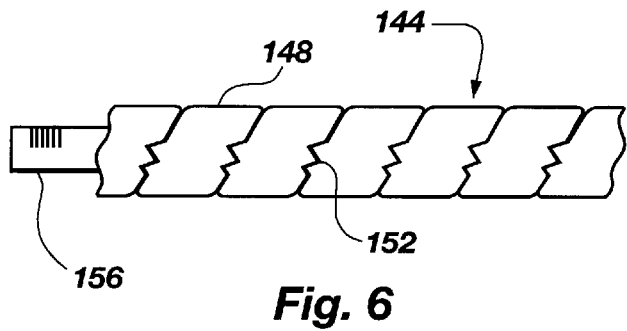
FIG. 6 is a side, fragmented view of a coil strip having interlocking teeth formed in adjacent edges of the strip, in accordance with the present invention.

FIG. 6 shows a side, fragmented view of a coil 144 formed of a strip of material 148 having teeth 152 formed on opposite edges of the strip, at selected locations therealong, so that when the strip is formed into the coil 144, the teeth intermesh or interlock to prevent relative rotation of adjacent windings, while allowing lateral flexibility. A core wire 156 is disposed in the hollow of the coil 144.

Figure 7:
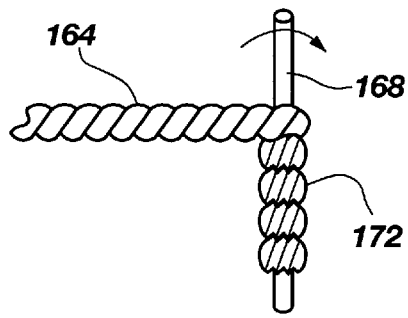
FIG. 7 illustrates diagrammatically a method of forming a coil from a threaded wire, in accordance with the present invention.

FIG. 7 illustrates the winding of a threaded wire 164 onto a mandrel 168 to form a coil guide wire 172 in which the threads of adjacent windings intermesh to inhibit relative rotation therebetween. The threads are simple screw threads and may be formed in a conventional manner.

Figure 8:
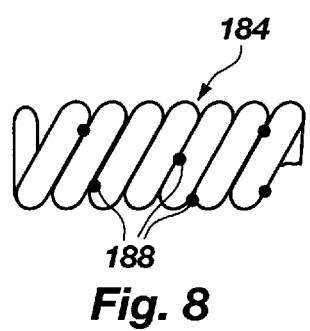
FIG. 8 is a side, fragmented view of a wire coil, showing selected adjacent windings spot welded together, in accordance with the present invention.

FIG. 8 shows a side, fragmented view of a coil guide wire 184 having spot welds 188 at selected locations along the coil to join the adjacent coils on either side of the spot welds and thereby prevent relative rotation therebetween. The spot welds 188 are spaced to allow the coil 184 to retain flexibility while also maintaining high torquability. No core wire would be required but may be desired with this embodiment.

Figure 9A:
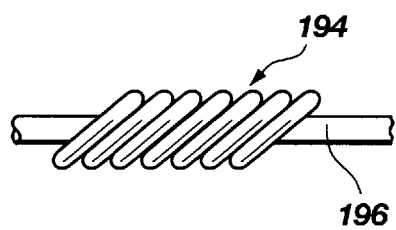
FIGS. 9A and 9B show respectively a side, fragmented view of a coil guide wire apparatus which has been canted, and an end view of the coil guide wire.
Figure 9B:
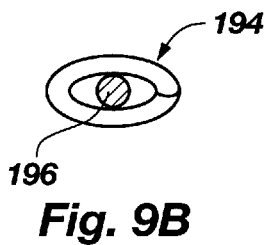

FIGS. 9A and 9B show respectively a side, fragmented view of a canted coil 194, and an end view thereof, with a center support wire 196 welded thereto. "Canting" of the coil transmits rotational force between adjacent windings which, along with the center wire 196, inhibits relative rotation therebetween, as desired.

Figure 10:
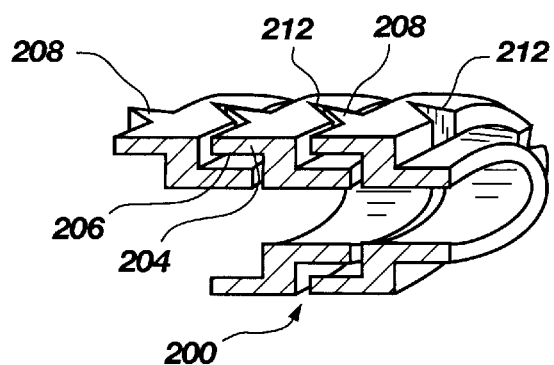
FIG. 10 shows a fragmented side, cross-sectional view, fragmented view of a coil wound from a strip of material having interlocking teeth, in accordance with the present invention.

FIG. 10 shows a specially formed strip 200 which when formed into a coil provides concentric lips 204 nesting in grooves 206 to prevent lateral or radial movement of adjacent coils relative to one another, and interlocking teeth 208 and gaps 212 to prevent relative rotational sliding of adjacent coils. The lips 204 and teeth 208 and gaps 212 serve to allow torque transmission, while maintaining concentricity of the coils without the need of a center wire.

In the embodiments of the guide wire discussed above, the guide wires can be made "flow directable" by providing highly flexible distal ends. "Flow directability" means that the distal end of the guide wire tends to "flow" with the blood around curves and bends in a vasculature passageway. To reduce resistance to movement of a guide wire in a vasculature passageway, the surface of the guide wire may be electropolished to increase the smoothness thereof, and additionally, a lubricious coating may be applied to the surface of the guide—such coatings might illustratively include silicon based oil and/or polymer or hydrophilic polymers. Alternatively, a lubricious sleeve made, for example, of a hydrophilic polymer could also be provided for disposal over the guide wire.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A catheter guiding implement for insertion into vasculature passageways and about which a catheter may be threaded for guidance through the passageways, said implement being torqueable in both a first and a second rotational direction, said implement comprising at least one strip of material generally circular in cross-section formed into an elongate coil having a plurality of windings and a central hollow, and coiled so that adjacent windings are generally in contact, and interlocking means comprising nesting indentations formed in a multiplicity of adjacent windings for inhibiting said adjacent windings from rotating relative to one another in a rotational direction tending to unwind said elongate coil, to thereby allow transmission of torque along the coil in both rotational directions, while also allowing flexure.

2. A catheter guiding implement as in claim 1 further including inhibiting means for inhibiting longitudinal separation of the windings.

3. A catheter guiding implement as in claim 1 wherein said inhibiting means comprise spot welds joining together adjacent windings at selected locations along the length of the coil.

4. A catheter guiding implement as in claim 2 wherein said inhibiting means comprises a core wire disposed in the hollow of the coil and joined to at least selected ones of the windings.

5. A catheter guiding implement as in claim 1 wherein said material is selected from the group consisting of platinum alloy, nickel-titanium alloy and stainless steel.

6. A catheter guiding implement as in claim 1 wherein said interlocking means comprises interlocking teeth formed in adjacent edges of the strip at least at selected locations along the coil.

7. A catheter guiding implement as in claim 6 wherein said adjacent edges formed with said teeth further comprise lips formed on one edge and corresponding grooves formed on an adjacent edge for receiving the lips to maintain alignment of the edges.

8. A catheter guiding implement as in claim 1 wherein said nesting indentations comprise nesting bends formed in at least selected adjacent windings of the coil to inhibit rotation of the windings relative to one another.

9. A catheter guiding implement as in claim 1 wherein said interlocking means comprises nesting ears formed in adjacent portions of the windings generally along the length of the coil.

10. A catheter guiding implement as in claim 1 wherein the strip of material is formed with threads generally along the length thereof such that the threads of adjacent windings nest together.

11. A catheter guiding implement as in claim 1 wherein said coil is canted generally along its length.

12. A catheter guiding implement as in claim 1 further including a core wire disposed in the hollow of the coil.

13. A catheter guiding implement as in claim 1 wherein said coil has a proximal end and a distal end, and wherein the distal end is curved.

14. A catheter guiding implement as in claim 13 further comprising a ball disposed in the distal end of the coil to serve as the leading end of the coil.

15. A catheter guiding implement as in claim 1 wherein the outside diameter of the coil is from about 0.008 inches to 0.090 inches.

16. A catheter guiding implement as in claim 1 wherein the thickness of the strip of material ranges from about 0.001 inches to 0.005 inches.

* * * * *